United States Patent [19]
Kiely et al.

[11] Patent Number: 5,599,977
[45] Date of Patent: Feb. 4, 1997

[54] OXIDATION PROCESS

[76] Inventors: Donald E. Kiely, 2521 Chatwood Rd., Birmingham, Ala. 35226; Andy Carter, 685-C Idlewild Cir., Birmingham, Ala. 35205; David P. Shrout, 27 Shades Crest Rd., Birmingham, Ala. 35226

[21] Appl. No.: 460,621

[22] Filed: Jun. 2, 1995

[51] Int. Cl.$^6$ ............ C07C 51/16; C07C 51/42
[52] U.S. Cl. .......... 562/523; 562/580; 562/582; 562/587; 562/590; 562/593
[58] Field of Search .................... 562/523, 580, 562/582, 587, 590, 593

[56] References Cited

U.S. PATENT DOCUMENTS

| | | | |
|---|---|---|---|
| 2,472,168 | 6/1949 | Mehltretter et al. | 260/523 |
| 3,078,140 | 2/1963 | Hatch | 23/1 |
| 4,478,722 | 10/1984 | Boom | 210/672 |

OTHER PUBLICATIONS

Brown, "Ion Exchange Chromatography . . . Ion Retardation Resin", Brown's 1995 Catalog, p. 37. 1995.
"Methods in Carbohydrate Chemistry", vol. II, Whistler et al. eds., pp. 38–40, 46, 48, Academic Press 1963.
CIBA, Ltd, Belg, Pat 615,023 (Sep. 1962). C.A. 1963, 2934b.
Bio–Rad, Inc Catalog (1995), pp. 37–39.
Mehltretter and Rist, "Sugar Oxidation", Ag. and Food Chem., 1, pp. 779–783 (1953).
Roper, "Selective Oxidation of Glucose", starch/starke 42 (1990) pp. 342–349.
Stanek et al., eds. "The Monosaccharides", pp. 741–752 Academic Press (1963).

*Primary Examiner*—Porfirio Nazario-Gonzalez
*Assistant Examiner*—Rosalynd A. William
*Attorney, Agent, or Firm*—Stephen Gates; Glenna Hendricks

[57] ABSTRACT

Rapid temperature rises which characterize carbohydrate-nitric acid oxidation reactions used to form carbohydrate-derived acids may be moderated and temperature control readily maintained by blowing a gas such as air, oxygen, nitrogen or the like into the reaction mixture as needed to control the temperature of the reaction. The more moderate reaction conditions afford higher yield of the desired product with a concomitant reduction of byproducts which may be difficult to remove and usually are unwanted as well. Upon completion the oxidation mixture is made basic (e.g. with an alkali metal base hydroxide or carbonate, ammonia or an amine) to a pH at which the the carboxyl group or groups of the product carbohydrate-derived acid are entirely in the salt form. The aqueous solution is then passed through an ion retardation resin column to recover the carbohydrate-derived salt, using water as the eluent. If desired, the carbohydrate-derived acid salt may then be recovered easily by removal of solvent water or by precipitation by addition of an water-miscible organic compound such as methanol, ethanol, acetone, isopropanol, etc.).

17 Claims, No Drawings

OXIDATION PROCESS

The present invention provides a convenient and improved process for the oxidation of organic compounds with nitric acid, in particular the oxidation of carbohydrates to aldonic or aldaric acids and their recovery.

BACKGROUND OF THE INVENTION

The preparation of organic acids by oxidation of compounds such as alcohols, esters, ethers, ketones or aldehydes with nitric acid often is characterized by violent or even explosively runaway reactions which have required extremely careful control of reaction conditions by cooling and/or stepwise addition of reactants. For example, the oxidation of aldoses, other monosaccharides, disaccharides, oligosaccharides or polysaccharides to aldonic or aldaric acids using nitric acid as the oxidizing agent according to typical procedures (J. Stanek, M. Cerny, J. Kocourek and J. Pacak, "The Monosaccharides", Academic Press, New York, 1963, p 744 and references 3–41 therein) is characterized by an exothermic step or steps in the early part of the oxidation (W. N. Haworth and W. G. M. Jones, *J. Chem. Soc.*, 1944, 65–7) that results in a rapid temperature rise (generally to 90° C. or higher) that is difficult to control by cooling. The threat of runaway and potentially explosive reaction mixtures, and concern for unwanted side reactions that cause lower yields of target aldonic or aldaric acids has created a need for a method for preventing the characteristic rapid and difficult to control reaction temperature rise. Preparation of aldonic and aldaric acids by nitric acid oxidation of carbohydrates and their isolation as their salts (for a review see J. Stanek op. cit.) dates back more than one hundred years. Among the most notable procedures for preparing aldaric acids are nitric acid oxidation procedures for preparing glucaric acid (isolated as the monopotassium salt)(H. Kiliani, *Ber.*, 58, 2344, 1925, 23–25% yield from starch; W. N. Haworth and W. G. M. Jones, *J. Chem. Soc.*, 65, 1944, 45% yield from glucose; C. L. Mehltretter, U.S. Pat. No. 2,436,659, Feb. 24, 1948, 41% from glucose; R. J. Bose, T. L. Hullar, B. A. Lewis and F. Smith, *J. Org. Chem.*, 26, 1300, 1961, 90 g of salt from 200 g of starch). Pilot scale nitric acid oxidation of glucose has been reported to give the same salt in yields of 40–43% (G. C. Mustakus, R. L. Slotter and R. L. Sipf, *Ind. Eng. Chem.*, 46, 427, 1954). Nitric acid oxidation of dextrose has been reviewed (C. L. Mehltretter and C. E. Rist, *Agric. and Food Chem.*, 1, 779, 1953). The monopotassium salt of glucaric acid was also isolated after catalytic oxidation of glucose (C. L. Mehltretter, C. E. Rist and B. H. Alexander, U.S. Pat. No. 2,472,168, Jun. 7, 1949, 54% from glucose).

Free aldaric acids generally have been prepared most conveniently by passing an aqueous solution of a salt over an ion exchange resin or, less so, by metathesis of an insoluble calcium or barium salt with dilute sulfuric acid.

Isolation of a single form of an aldaric acid from the equilibrium mixture of forms (acyclic diacid, multiple acid/lactone, dilactone) which are characteristic of acidic solutions of these acids has been a significant problem associated with preparing aldaric acids by carbohydrate oxidation. Among aldaric acids, galactaric acid is unusual in that it is easy to isolate because a single form dominates the equilibrium mixture and readily crystallizes from aqueous solutions. On the other hand, although glucaric acid forms a somewhat water insoluble monopotassium salt, isolations from glucose oxidations typically are in the 40% range. At the pH where this latter precipitation occurs, the desired monopotassium salt form may be in equilibrium with other salt/acid forms of glucaric acid, which perhaps limits the amount of glucaric acid that is available. Aldonic and aldaric acids tend to form insoluble salts with divalent cations such as calcium and barium but aldaric salts of divalent cations in general have not been isolable as products from nitric acid oxidation of carbohydrates in high enough purity for such a process for their isolation to be practical. For example, calcium glucarate is much more readily prepared from purified monopotassium glucarate than it is directly from a nitric acid oxidation procedure.

Glucaric acid is not presently available on an industrial scale because there is no economic process available (H. Roper, *Starch/Starke*, 42, 346, 1990). D-glucose (commonly referred to as glucose or dextrose) is a significant commercial product available from starch hydrolysis. Therefore the ability to use glucose as an inexpensive precursor for the corresponding aldaric acid, glucaric acid, in a commercial process would be desirable. A number of uses for glucaric acid have been reported and the commercial availability of comparatively inexpensive glucaric acid could give rise to additional uses. Similarly, other aldonic and aldaric acids which are not presently available commercially might also find applications if the acids could be conveniently prepared from appropriate carbohydrate sources.

Techniques reported to assist in controlling the temperature of a glucose oxidation (60°–64° C.) have included adding a significant amount of sodium nitrite to the reaction (CIBA Ltd., Belgian Patent 615,023, Sep. 13, 1962, yield of monopotassium salt was 46.0–48.5%) or adding the glucose to concentrated nitric acid over a period of time (C. L. Mehltretter, *Methods Carbohydr. Chem.*, 2, 46 (1963); yield of the monopotassium salt was 41%).

Recovery of glucaric acid in forms other than as the monopotassium salt were described even early in this century (see *Beilstein's Handbuch der Organischen Chemie*, Vierte Auflage, covering the literature until Jan. 1, 1910). More recently glucaric acid lactone salts have been reported (alkali, alkaline earth or ammonium salts of D-glucaric acid 1,4-lactone, E. F. J. Thorpe, German Patent 1,081,443, May 12, 1960). The monopotassium salt form of glucaric acid was also isolated after catalytic oxidation of glucose (C. L. Mehltretter, C. E. Rist and B. H. Alexander, U.S. Pat. No. 2,472,168, Jun. 7, 1949; 54% from glucose). Also difficulties often have been encountered in converting various salts to other salts. Therefore there has been a need for a method for the facile recovery of aldonic and aldaric acid salts.

SUMMARY OF THE INVENTION

Passing a gas through the reacting mixture affords good temperature control of the nitric acid oxidation of saccharides and polysaccharides to aldonic or aldaric acids. Salt forms of the acids are recovered from nitric acid oxidation product mixtures after completion of the reaction by adjusting the reaction mixture to pH>7, passing the basic solution over an ion retardation column and eluting the salt of the aldonic or aldaric acid with water. The aqueous salt solution may then be used directly for further procedures or, if desired, the salt may then be recovered by evaporating the solution to dryness. The aldonic or aldaric acid may be recovered, if desired, by passing a solution of the salt over an acid form ion exchange resin.

DETAILED DESCRIPTION OF THE INVENTION

It now has been found that the rapid temperature rises which characterize carbohydrate-nitric acid oxidation reactions used to form carbohydrate-derived acids may be moderated and temperature control readily maintained by blowing a gas such as air, oxygen, nitrogen or the like into the reaction mixture as needed to control the temperature of the reaction. This technique allows the reaction temperatures to be conveniently held at a desired temperature such as 60° C. or less during the oxidation procedure, thereby limiting the threat of a runaway reaction associated with higher reaction temperatures. In addition, the more moderate reaction conditions afford higher yield of the desired product with a concomitant reduction of byproducts which may be difficult to remove and usually are unwanted as well. The method of the invention in some fashion prevents undesirable spontaneous temperature rises associated with these oxidations. The exact mechanism by which the temperature is controlled by passage of a gas through the mixture in these oxidations is not clearly understood however.

Upon completion of a carbohydrate oxidation, in particular with nitric acid, the oxidation mixture is made basic (e.g. with an alkali metal base such as sodium hydroxide, potassium hydroxide, sodium carbonate, potassium carbonate and the like, or ammonia or an amine) to a pH at which the the carboxyl group or groups of the product carbohydrate-derived acid are entirely in the salt form. The aqueous solution is then passed through an ion retardation resin column, using water as the eluent. The target acid salt typically elutes first, lesser amounts of colored materials typically elute next, finally followed by inorganic salts (e.g. nitrates). In cases where both monobasic and dibasic salts such as aldonic and aldaric acid salts are present, the aldonic acid salt elutes first. If desired, the carbohydrate-derived acid salt may then be recovered easily by removal of solvent water or by precipitation by addition of an water-miscible organic compound such as methanol, ethanol, acetone, isopropanol, etc.).

Ion retardation resins such as AG 11 A 8 (BioRad) have been developed to provide a means for desalting organic solutions. The AG 11 A8 resin is made by absorbing acrylic acid on a cross-linked amino substituted styrene/divinylbenzene resin and polymerizing the acrylic acid to produce spherical resin beads containing paired anion and cation exchange sites. When the resin is free of absorbed salts the carboxyl and ammonium groups of the polymers form each others counterions. These sites form weak interactions with mobile cations and anions leading to their (weak) absorption. During elution with water the absorbed salts move down the column as their ions are repeatedly absorbed and desorbed and are thus retarded. As materials are eluted from the column the eluting liquid usually shows the schlieren effect (regions of varying refractive index) which allows separation of the fractions. The eluting liquid also may be monitored for its ion conductivity in order to determine when the various ionic materials are being discharged from the column.

Examples of applications which have been proposed for ion retardation resins include removal of salts from protein hydrolyzates, removal of ammonium salts from enzymes, desalting urinary amino acids, separation of albumin from salts, removal of SDS from proteins, separation of electrolytes from non-electrolytes, adsorption of mineral acids, and separation of metals (Section 6, 1995 Catalog, BioRad, Inc.). The process employing an ion retardation resin in the workup of carbohydrate-nitric acid oxidation products differs markedly from processes using ion exchange resins, gel filtration, deionization or ion exclusion. The ion retardation process is very simple since the only eluent is water, the desired acid salts do not have to be stripped from the resin with base (which then itself requires removal), and post resin treatment is not required to get the acid in the desired salt form. For example, a procedure that uses ion exchange resin to recover aldaric acid salts after nitric acid oxidation of appropriate carbohydrates is described in Jansen and Samuelson (J. Chromatogr., 57, 353, 1971). In Jansen, after oxidation of aldoses with nitric acid, a basic anion exchange resin (acetate form) is employed to remove nitric acid from the oxidation mixture. Then the resin is eluted with aqueous base (magnesium acetate/acetic acid) to release the carbohydrate acid(s). The effluent is then treated with a cation exchange resin (H+ form) to neutralize acetate, acetic acid is evaporated, and the residue of carbohydrate acid(s) treated with sodium hydroxide to convert the acid(s) to the salt form. The latter is then subjected to further anion exchange chromatography for additional purification.

Further, the method of the present invention may be used for the recovery of water-soluble salts of aldonic acids such as gluconic acid and the like, aldaric acids such as glucaric acid, xylaric acid and the like, uronic acids such as glucuronic acid, maltobiuronic acid, pectic acid and alginic acid and the like, heparin, chondroitin sulfate and related glycosaminoglycans and other acids derived from carbohydrates in general such as tartaric acid, citric acid, saccharinic acid, isosaccharinic acid, metasaccharinic acid and the like, from aqueous solutions containing inorganic salts, whether the desired carbohydrate acid salts have been prepared using chemical or non-chemical (such as microbiological) methods. The method of the present invention also affords the possibility to recover aldaric acids directly in certain desirable monosalt forms (e.g. mono sodium or mono potassium glucarate) from a solution containing other inorganic salts by first neutralizing the oxidation mixture to the appropriate pH and then applying the solution to the resin as described for the disalts.

EXPERIMENTAL

Example 1

α-D-Glucose (25.0 g, 138.4 mmol, A.C.S. Reagent Grade, 0.2% Drying Loss, Aldrich) was added to a 500 mL round-bottomed flask containing $HNO_3$ (26.4 mL, 415.2 mmol, density 1.4134 g/mL, A.C.S. Reagent 70% w/w, Fisher). The mixture, with stirring, was then heated to 44° C. to dissolve the glucose, after which the heat was removed. Oxygen then was bubbled into the solution for 10 seconds using a 5 mL pipet as the delivery device. This brief bubbling was performed in order to determine that the oxygen delivery system was functioning properly. Then a few crystals of sodium nitrite were added to the solution in order to initiate the reaction. Within a few minutes the solution started to warm and gave off a large volume of brown gases. When the liquid temperature reached approximately 46° C. oxygen flow into the mixture was begun and adjusted to maintain the temperature between 44°–48° C. After 50 minutes the temperature began to decrease. When the temperature had fallen to 40° C. the reaction mixture was placed in a preheated 45° C. oil bath. The reaction continued to produce brown gases, so an intermittent flow of oxygen was used to keep the solution free of gases. The production of gases continued for 4.25 h. When gas production ceased the reaction mixture was placed on a rotary evaporator where a small amount of water (~15 mL) was removed. The reaction mixture then was placed back in the 45° C. oil bath and more $HNO_3$ (8.9 mL, 138.4 mmol) was added. The reaction again started producing brown gases and the temperature began to rise. This was controlled as before with an intermittent flow of oxygen. The rise in temperature lasted for 30 min and the production of brown gases lasted for 4 h. At that time the oxidation was deemed to have been completed.

The reaction product was recovered as follows:

The reaction mixture was transferred to a beaker (400 mL), and cooled in an ice bath with stirring. Aqueous sodium hydroxide (12M) was slowly added with stirring to the cooled reaction mixture until pH10 was obtained (pH meter). The solution was kept in a refrigerator (ca. 5° C.) overnight (ca. 10 h), by which time the pH had dropped to approximately 8. The solution was then passed through a column containing ion retardation resin (Bio-Rad AG$^R$11A8, vol 502 mL, 4 cm×40 cm) using water as the eluent. The disodium salt product was contained in the fractions collected between 200–800 mL. The combined fractions were concentrated at reduced pressure to a thick syrup which was then triturated with alcohol (methanol or ethanol) until the product solidified as a fine powder, which was collected by filtration and dried (30.2 g, 85.9%). The product was found to be substantially pure disodium glucarate when examined by $^{13}$C NMR.

Comparative Example

The oxidation of Example 1 was repeated without using a cooling gas as follows. α-D-Glucose (25.0 g, 138.4 mmol, A.C.S. Reagent Grade, 0.2% Drying Loss, Aldrich) was added to a 500 mL round-bottomed flask containing HNO$_3$ (26.4 mL, 415.2 mmol, density 1.4134 g/mL, A.C.S. Reagent 70% w/w, Fisher). The mixture, with stirring, was then heated to 44° C. to dissolve the glucose, after which the heat was removed. Then a few crystals of sodium nitrite were added to initiate reaction. Within a few minutes the solution began to warm spontaneously and emit a large volume of brown gases. Within a matter of seconds the gas evolution increased significantly and the temperature of the reaction rose to 90°–100° C. The flask was quickly transferred to an ice bath where the temperature was reduced to about 60° C. (cooling required about 20 min). The reaction mixture then was removed from the ice bath and replaced in the 45° oil bath and more HNO$_3$ (8.9 mL, 138.4 mmol) was added. The mixture once again began to emit brown gases and was allowed to remain in the oil bath for 4 hours to complete the oxidation. The product was then recovered using the method of Example 1. The product (27.4 g, 77.9%) was examined by $^{13}$C NMR and was judged to be somewhat less pure than the product obtained in Example 1.

A comparison of the results of the above Examples shows that the use of a cooling gas affords a significantly better yield and purer product than the method of the prior art.

Haworth and Jones, *J. Chem. Soc.*, 1944, 65–67, obtained glucosaccharic (glucaric) acid as its monopotassium salt in 45% yield by the oxidation of glucose with nitric acid without bubbling gas into the reaction mixture. Mehltretter U.S. Pat. No. 2,436,659 likewise obtained a maximum yield of 41%. The process disclosed in CIBA Belgian Patent 615,023 afforded glucaric acid as its monopotassium salt in up to 48.5% yield. Clearly the process of the present invention has essentially doubled the yield of desired product over that of the processes of the prior art.

Example 2

In this Example the amount of gas required for reaction mixtures of various sizes and the use of different gases to control the oxidation reaction were examined.

a) α-D-Glucose (25 g, 138.4 mmol) was added to a 500 mL round-bottomed flask containing HNO$_3$ (26.4 mL, 415.2 mmol). The mixture was stirred to dissolve the glucose. After the glucose had dissolved a typical yellow color appeared in the liquid phase and brown gases appeared in the vapor headspace of the flask, soon followed by an exotherm. After 14 minutes the liquid temperature had reached 40° C. Oxygen then was bubbled into the liquid phase through an ebullator at a rate of about 50 ft$^3$/h. Within 1 minute 40 seconds the temperature had dropped to 34° C. As the strength of the exotherm decreased, the rate of gas flow was decreased. This cooling was sufficient to cool the exotherm throughout the first stage of the oxidation.

b) α-D-Glucose (50 g, 276.8 mmol) was added to a 500 mL round-bottomed flask containing HNO$_3$ (52.8 mL, 830.4 mmol). The mixture was stirred to dissolve the glucose. After the glucose had dissolved the typical yellow color appeared in the liquid phase and brown gases appeared in the vapor headspace of the flask, soon followed by an exotherm. When the liquid temperature had reached 41° C. oxygen was bubbled into the liquid phase through an ebullator. It was necessary to use a rate of about 80 ft$^3$/h to control the reaction. Within 2 minutes 5 seconds the temperature had dropped to 36° C. As the strength of the exotherm decreased, the rate of gas flow was decreased. This cooling was sufficient to cool the exotherm throughout the first stage of the oxidation.

c) α-D-Glucose (25 g, 138.4 mmol) was added to a 500 mL round-bottomed flask containing HNO$_3$ (26.4 mL, 415.2 mmol). The mixture was stirred to dissolve the glucose. After the glucose had dissolved a typical yellow color appeared in the liquid phase and brown gases appeared in the vapor headspace of the flask, soon followed by an exotherm. When the exotherm reached 41° C. nitrogen was bubbled into the liquid phase through an ebullator at a rate of about 30 ft$^3$/h. One minute later the temperature remained at 41° C. Then the nitrogen flow was raised to 50 ft$^3$/h. Within 1 minute 5 seconds the temperature had dropped to 36° C. As the strength of the exotherm decreased, the rate of nitrogen flow was decreased. As in the other runs in this Example, this cooling was sufficient to cool the exotherm throughout the first stage of the oxidation.

d) a) α-D-Glucose (25 g, 138.4 mmol) was added to a 500 mL round-bottomed flask containing HNO$_3$ (26.4 mL, 415.2 mmol). The mixture was stirred to dissolve the glucose. After the glucose had dissolved a typical yellow color appeared in the liquid phase and brown gases appeared in the vapor headspace of the flask, soon followed by an exotherm. When the liquid temperature had reached 40° C. compressed air was bubbled into the liquid phase through an ebullator at a rate of about 50 ft$^3$/h. Within 42 seconds the temperature had dropped to 36° C. As the strength of the exotherm decreased, the rate of gas flow was decreased. This cooling was sufficient to cool the exotherm throughout the first stage of the oxidation.

It can be seen from this Example that the use of nitrogen or air in place of oxygen affords the same effective control of the oxidation reaction. Likewise, this Example demonstrates, depending on the quantity of material being oxidized, the rate of gas flow required to effect good control will vary.

Example 3

Delta gluconolactone (25.0 g, 140.3 mmol, Aldrich, 99%) was added to a 500 mL round-bottomed flask containing HNO$_3$ (17.9 mL, 280.6 mmol, density 1.4134 g/mL, A.C.S.

Reagent 70% w/w, Fisher). The mixture, with stirring, was then heated to 44° C. and water was added (7 mL) to dissolve the gluconolactone, after which the heat was removed. A few crystals of sodium nitrite were added to the solution to initiate the reaction. The reaction mixture was placed in a preheated 50° C. oil bath and stirred at 50° C. for 2.5 h. No spontaneous temperature rise was observed, but oxygen gas was bubbled through the reaction mixture periodically to purge the solution of brown gases. The solution was concentrated at reduced pressure to a thick syrup. Nitric acid (8.9 mL, 140.3 mmol, density 1.4134 g/mL) was added to the syrup and the solution was kept at 50° C. for an additional 3.5 h, brown gases being purged as above with oxygen.

The acid disodium salt isolation procedure employed was identical to that described in Example 1. The isolated yield was 30.0 g (84.2%).

Mehltretter and Rist, *Agric. and Food Chem.*, 1, 779–83 (1953) obtained a 44% yield of glucaric acid as its monopotassium salt from the nitric acid oxidation of gluconolactone without bubbling gas through the reacting mixture. The process of the present invention affords nearly double the yield of the method of the prior art.

Example 4

D-Xylose (25.0 g, 166.5 mmol, Aldrich, 99+) was oxidized as described in Example 1. The amount of nitric acid used at the beginning of the procedure was 31.8 mL (499.5 mmol), the amount added in the latter part of the oxidation was 10.6 mL $HNO_3$ (166.5 mmol).

Half of the oxidation mixture was used for isolation of the disodium salt. The reaction mixture was transferred to a beaker (400 mL) and cooled in an ice bath with stirring. Aqueous sodium hydroxide (12M) was slowly added with stirring to the cooled reaction mixture to pH10 (pH meter). The solution was kept in a refrigerator (ca. 5° C.) overnight (ca. 10 h) by which time the pH had dropped to approximately 8. The solution was then passed through a column containing ion retardation resin (Bio-Rad AG$^R$11A8, vol 502 mL, 4 cm×40 cm) using water as the eluent. The disodium salt product was contained in the fractions collected between 200–600 mL. The combined fractions were concentrated at reduced pressure to a thick syrup which was then triturated with alcohol (ethanol) until the product solidified as a fine powder, which was collected by filtration and dried (15.5 g, 83.1%, based on 12.5 g of xylose).

Cantrell et al., *J. Org. Chem.*, 42, 3562 (1977) prepared xylaric acid by nitric acid oxidation of xylose by oxidation of xylose with nitric acid without bubbling gas through the reaction and obtained a 44% yield of xylaric acid. It is clear that the method of the present invention affords nearly twice the yield of the prior art method.

Example 5

D-Xylose (10.0 g, 66.6 mmol) was oxidized as in Example 3 but with proportionally smaller amounts of nitric acid; 12.7 mL (199.8 mmol) and then 4.24 mL (66.6 mmol). The reaction mixture was transferred to a beaker (400 mL) and cooled in an ice bath with stirring. Aqueous potassium hydroxide (12M) was slowly added with stirring to the cooled reaction mixture to pH 10 (pH meter). The solution was kept in a refrigerator (ca. 5° C.) overnight (ca. 10 h) by which time the pH had dropped to approximately 8. The solution was then passed through a column containing ion retardation resin (Bio-Rad AG$^R$11A8, vol 502 mL, 4 cm×40 cm) using water as the eluent. The product disalt was contained in the fractions collected between 200–600 mL. The combined fractions were concentrated at reduced pressure to a thick syrup which was then triturated with alcohol (ethanol) until the product solidified as a fine powder, which was collected by filtration and dried (14.4 g, 84.5%). It is clear that the recovery process is as effective for the dipotassium salt as it is for the disodium salt.

Example 6

α-D-Glucose (25.0 g, 138.4 mmol, A.C.S. Reagent Grade, 0.2% Drying Loss, Aldrich) was added to a 500 mL round-bottomed flask containing $HNO_3$ (26.4 mL, 415.2 mmol, density 1.4134 g/mL, A.C.S. Reagent 70% w/w, Fisher). The mixture, with stirring, was then heated to 44° C. to dissolve the glucose, after which the heat was removed. Oxygen then was bubbled into the solution for 10 seconds using a 5 mL pipet as the delivery device. Then a few crystals of sodium nitrite were added to the solution in order to initiate the reaction. Within a few minutes the solution started to warm and gave off a large volume of brown gases. When the liquid temperature reached approximately 46° C. oxygen flow into the mixture was begun and adjusted to maintain the temperature between 44°–48° C. and to assist in the removal of the brown gases. After 40 minutes the gas flow was stopped and the flask was placed in an ice bath.

Sodium gluconate (26.0 g, 86.2%) was recovered using the procedure of Example 1. Examination of the product by $^{13}C$ NMR showed the presence of a minor amount of disodium glucarate. More careful monitoring of the effluent from the ion exclusion column would allow recovery of purer product.

Example 7

Glucaric acid (from 10 g monopotassium glucarate, 40.2 mmol) I concentrated nitric acid (70% w/w, 20.1 mmol) was cooled in an ice bath with stirring. Aqueous ammonium hydroxide (14.8M) was slowly added with stirring to the cooled solution until pH10 (pH meter) was attained. The solution was kept at room temperature for 4 hours, by which time the pH has dropped to 8.6. The solution was then passed through a column containing ion retardation resin (BioRad AG11A®, vol 502 mL, 4 cm×40 cm) using water as the eluent, and the fractions containing the disalt were combined and concentrated at reduced pressure to a thick syrup which was triturated with acetone until it solidified as a fine powder. The powdered diammonium glucarate was collected by filtration and dried (9.0 g, 91.7%).

We claim:

1. In the process of oxidizing a carbohydrate with nitric acid to form a carbohydrate-derived acid the improvement which comprises a) blowing a gas, selected from air, oxygen or nitrogen, into the reacting mixture of nitric acid and precursor carbohydrate at a rate sufficient to maintain the reaction mixture at a desired temperature, b) after the oxidation has been completed, neutralizing the acid mixture with a base selected from the group consisting of alkali metal hydroxides, alkali metal carbonates, ammonia and amines to a pH sufficient to convert the contained acids to their salts, c) passing the resulting solution of salts through a column containing an ion retardation resin, d) eluting the column with water, and e) collecting the portion of effluent which contains the salt of the desired carbohydrate-derived acid.

2. The process of claim 1 wherein the carbohydrate precursor is glucose and the carbohydrate-derived acid is glucaric acid.

3. The process of claim 1 wherein the carbohydrate precursor is glucose and the carbohydrate-derived acid is gluconic acid.

4. The process of claim 1 wherein the carbohydrate precursor is xylose and the carbohydrate-derived acid is xylaric acid.

5. The process of claim 1 wherein the carbohydrate precursor is starch and the carbohydrate-derived acid is glucaric acid.

6. The process of claim 1 wherein the ion retardation resin comprises paired carboxyl and ammonium groups.

7. A process for purifying a water-soluble salt of a carbohydrate-derived acid contained in an aqueous solution which comprises a) passing the solution containing the salt through a column containing an ion retardation resin, b) eluting the column with water, and c) collecting the portion of effluent from the column which contains the salt of the carbohydrate-derived acid.

8. The process of claim 7 wherein the carbohydrate-derived acid is glucaric acid.

9. The process of claim 7 wherein the carbohydrate-derived acid is gluconic acid.

10. The process of claim 7 wherein the carbohydrate-derived acid is citric acid.

11. The process of claim 7 wherein the carbohydrate-derived acid is xylaric acid.

12. The process of claim 7 wherein the ion retardation resin comprises paired carboxyl and ammonium groups.

13. In the process of oxidizing a carbohydrate with nitric acid to form a carbohydrate-derived acid the improvement which comprises blowing a gas into the reacting mixture of nitric acid and precursor carbohydrate at a rate sufficient to maintain the reaction mixture at a desired temperature.

14. The process of claim 13 wherein the carbohydrate precursor is glucose and the carbohydrate-derived acid is glucaric acid.

15. The process of claim 13 wherein the carbohydrate precursor is glucose and the carbohydrate-derived acid is gluconic acid.

16. The process of claim 13 wherein the carbohydrate precursor is xylose and the carbohydrate-derived acid is xylaric acid.

17. The process of claim 13 wherein the carbohydrate precursor is starch and the carbohydrate-derived acid is glucaric acid.

* * * * *